United States Patent
Harrand et al.

(10) Patent No.: US 11,285,046 B2
(45) Date of Patent: Mar. 29, 2022

(54) NONLINEAR PASSIVE HEARING PROTECTION DEVICE AND METHOD

(71) Applicant: CFD Research Corporation, Huntsville, AL (US)

(72) Inventors: Vincent Johannes Harrand, Huntsville, AL (US); David Keith Sedberry, Jr., Huntsville, AL (US); Phillip Edward Whitley, Miami, FL (US); Xiangguang Gary Tan, Alexandria, VA (US); Andrzej Przekwas, Huntsville, AL (US)

(73) Assignee: CFD Research Corporation, Huntsville, AL (US)

( * ) Notice: Subject to any disclaimer, the term of this patent is extended or adjusted under 35 U.S.C. 154(b) by 760 days.

(21) Appl. No.: 15/710,646

(22) Filed: Sep. 20, 2017

(65) Prior Publication Data
US 2019/0083319 A1  Mar. 21, 2019

(51) Int. Cl.
*A61F 11/08* (2006.01)

(52) U.S. Cl.
CPC ......... *A61F 11/08* (2013.01); *A61F 2011/085* (2013.01)

(58) Field of Classification Search
CPC .... A61F 11/08; A61F 2011/085; A61F 11/00; A61F 11/008; A61F 11/06; A61B 17/00; H04R 25/02; H04R 1/1016; H04R 2225/025; H04R 25/65; H04R 25/652;
(Continued)

(56) References Cited

U.S. PATENT DOCUMENTS

| 5,631,965 A * | 5/1997 | Chang ..................... A61F 11/08 |
| | | 381/72 |
| 6,082,485 A * | 7/2000 | Smith ..................... A61F 11/08 |
| | | 128/868 |

(Continued)

FOREIGN PATENT DOCUMENTS

| EP | 0835042 A2 * | 4/1998 | ........... H04R 25/654 |
| EP | 3260491 A1 * | 12/2017 | ............ C08L 53/025 |

OTHER PUBLICATIONS

EP-0835042-A2 machine translation (Year: 2020).*
(Continued)

*Primary Examiner* — Caitlin A Carreiro
(74) *Attorney, Agent, or Firm* — Maschoff Brennan; Jonathan M. Benns

(57) ABSTRACT

A passive non-linear earplug can include: a tapered body having a channel extending from a wider distal end to a narrower proximal end, the tapered body having shape memory and size adapted for being received into an ear canal of a human subject; and a disk attached to the wider distal end of the tapered body, the disk having one or more holes aligned with the channel. A structural tube can be located in the channel. A handle can be attached to the tapered body and/or disk. An annular member can be coupled to the disk opposite of the tapered body, the annular member having an aperture that at least partially aligns with the channel. A tube member can be coupled to the disk opposite of the tapered body. The earplug can attenuate loud sounds while allowing normal sounds to be heard, which provides for the non-linearity.

20 Claims, 10 Drawing Sheets

(58) Field of Classification Search
CPC . H04R 25/654; H04R 25/658; H04R 2460/11
USPC ........ 128/864–868; D24/106; 381/23.1, 312, 381/328, 72, 380; D29/108, 112; 181/129, 130, 135
See application file for complete search history.

(56) References Cited

U.S. PATENT DOCUMENTS

| | | | | |
|---|---|---|---|---|
| 6,148,821 | A * | 11/2000 | Falco | H04R 1/1016 128/864 |
| 8,820,470 | B2 * | 9/2014 | Brown | A61F 11/12 181/135 |
| 2012/0318605 | A1 * | 12/2012 | Brown | A61F 11/12 181/126 |

OTHER PUBLICATIONS

Murphy, WJ, et al., "Measurement of impulse peak insertion loss for four hearing protection devices in field conditions", International Journal of Audiology 2012; 51: S31-S42.

Nakashima, A, "Comparison of different types of hearing protection devices for use during weapons firing", Journal of Military, Veteran and Family Health, 1(2) 2015 doi: 10.3138/jmvfh.3076.

Khan, A, et al., "Comparison of Two Acoustic Test Fixtures for Measurement of Impulse Peak Insertion Loss", EPHB Report No. 350-13a, NIOSH.

* cited by examiner

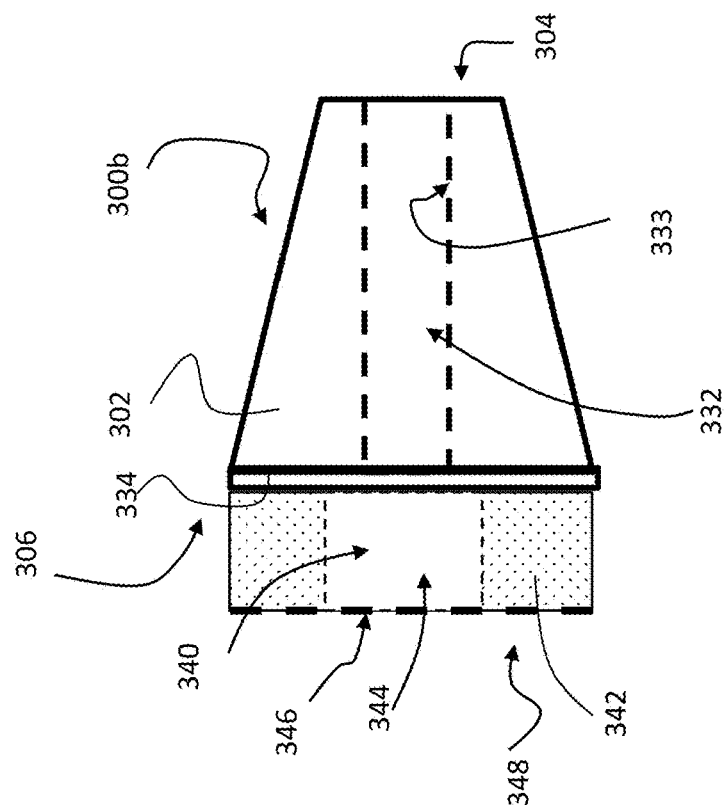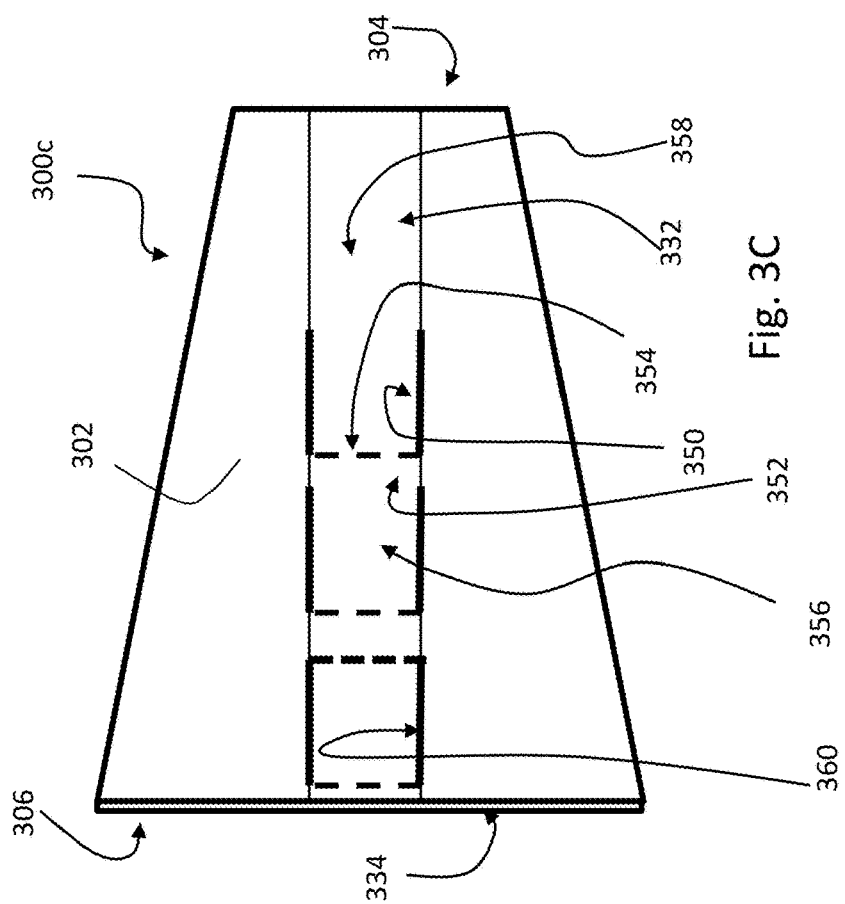

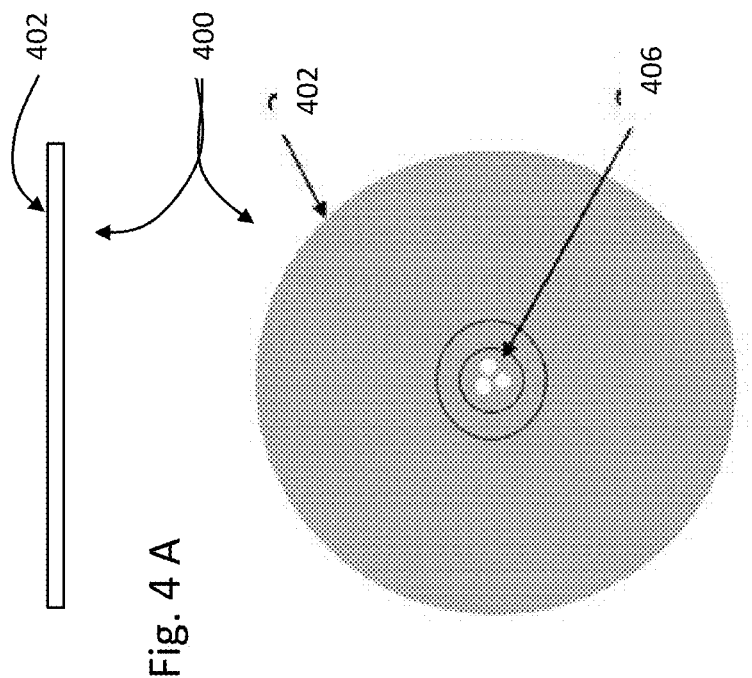
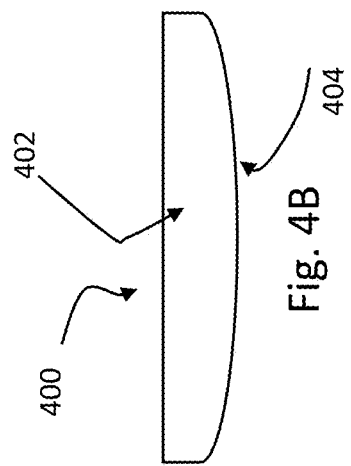
Fig. 4

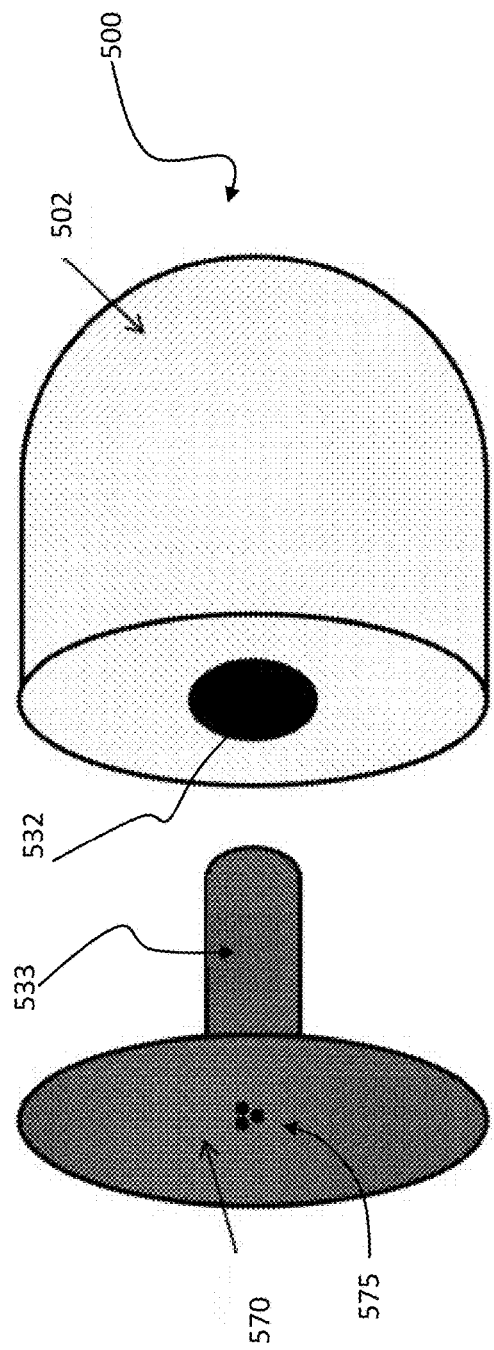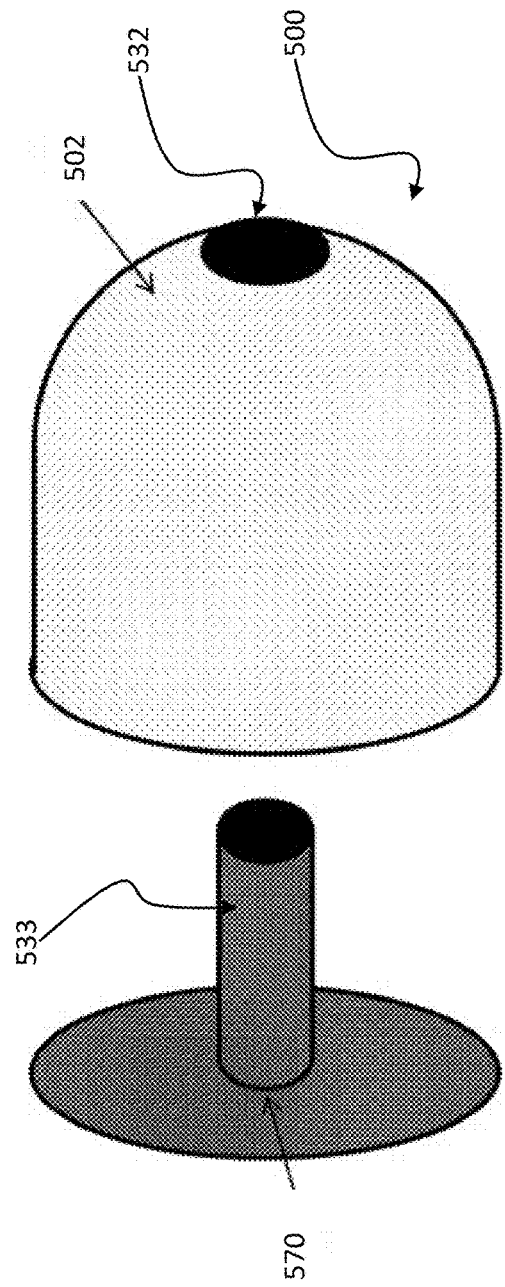

NONLINEAR PASSIVE HEARING PROTECTION DEVICE AND METHOD

GOVERNMENT RIGHTS

This invention was made with government support under contract W31P4Q-12-C-0158 awarded by the Defense Advanced Research Projects Agency (DARPA). The government has certain rights in the invention.

BACKGROUND

Known hearing protection systems can be categorized as follows. Ear muffs fit around the ear and provide protection by covering the ear, while earplugs fit into the ear canal and provide protection by blocking the ear canal only. A second distinction can be made for passive versus active devices. An active device uses electronic circuits for sound attenuation and filtering, while a passive device does not use electronics to attenuate the sound, but instead uses physics based principles for materials and structures (e.g., non-automated) to reduce the sound level in the ear. The disadvantage of an active device is that it requires built-in electronics, batteries and is much more expensive than a passive device. A third distinction applies to the specific sound attenuation characteristics of the device, such as whether it blocks all sounds (e.g., foam earplugs), or blocks some sound but maintains neutral frequency characteristics (e.g., hi fidelity—HiFi ear protection devices for musicians), or blocks very loud impulsive sounds only (e.g., level-dependent, non-linear ear protection devices), while other not-so-loud sounds are allowed to pass through for maintaining situational awareness.

A number of different hearing protection devices are known. Specifically, for the category of level-dependent, non-linear passive earplugs, there are several existing patents that provide the background for the technology. For example, U.S. Pat. No. 6,148,821 discloses a device for selective nonlinear attenuating earplugs, while another U.S. Pat. No. 7,697,706 is for low sound attenuating hearing protection devices. They are all based on the principle of restricting sound transfer to the ear drum through an orifice (U.S. Pat. Nos. 6,148,821 and 6,608,079), a resonator (U.S. Pat. No. 5,113,967), a diaphragm (U.S. Pat. No. 8,744,111), or combination (U.S. patent application Ser. No. 14/340, 599), but they differ significantly in design, layout, and ultimately performance.

SUMMARY

In one embodiment, a passive non-linear earplug can include: a tapered body having a channel extending from a wider distal end to a narrower proximal end, the tapered body having shape memory and size adapted for being received into an ear canal of a human subject; and a disk attached to the wider distal end of the tapered body, the disk having one or more holes aligned with the channel. In one aspect, a structural tube is located in the channel. In one aspect, the structural tube is coupled or integrated with the disk. In one aspect, a handle is attached to the tapered body and/or disk. In one aspect, an annular member is coupled to the disk opposite of the tapered body, the annular member having an aperture that at least partially aligns with the channel. In one aspect, a tube member is coupled to the disk opposite of the tapered body, the tube member having a lumen that at least partially aligns with the channel. In one aspect, the tube member includes one or more lateral apertures fluidly communicated with the lumen. In one aspect, the disk includes a proximal side that is attached to the distal end of the tapered body, and includes a distal side that is planar. In one aspect, the disk includes a proximal side that is attached to the distal end of the tapered body, and includes a distal side that is non-planar.

In one embodiment, the disk includes a proximal side that is attached to the distal end of the tapered body, and includes a distal side. In one aspect, the earplug further includes: an annular ring having a proximal side attached to the distal side of the disk so that an aperture of the annular ring is at least partially aligned with the holes of the disk; and a second disk attached to a distal side of the annular ring, the second disk having one or more second holes aligned with the holes of the disk. In one aspect, the earplug can include: a second annular ring having a proximal side attached to a distal side of the second disk so that a second aperture of the second annular ring is at least partially aligned with the second holes of the second disk; and a third disk attached to a distal side of the second annular ring, the third disk having one or more third holes aligned with the second holes of the second disk. In one aspect, a handle is attached to a distal side of the second disk. In one aspect, a handle is attached to a distal side of the third disk.

In one embodiment, a kit can include: a plurality of tapered bodies, each having a channel extending from a wider distal end to a narrower proximal end, each tapered body having shape memory and size adapted for being received into an ear canal of a human subject; and two or more acoustic filter caps, each acoustic filter cap being adapted to couple with one of the tapered bodies. In one aspect, each acoustic filter cap can include: a disk having a structural tube extending from a proximal side and having one or more holes therethrough and with a lumen of the structural tube, the structural tube being adapted to be aligned with the channel of a tapered body when the acoustic filter cap is attached thereto. In one aspect, each acoustic filter cap can include: an annular ring having a proximal side attached to a distal side of the disk so that an aperture of the annular ring is at least partially aligned with the holes of the disk; and a second disk attached to a distal side of the annular ring, the second disk having one or more second holes aligned with the holes of the disk. In one aspect, each acoustic filter cap can include: a second annular ring having a proximal side attached to a distal side of the second disk so that a second aperture of the second annular ring is at least partially aligned with the second holes of the second disk; and a third disk attached to a distal side of the second annular ring, the third disk having one or more third holes aligned with the second holes of the second disk.

In one embodiment, a method of hearing protection can include: providing two passive non-linear earplugs of any of the embodiments or obtained from any of the kits; inserting the tapered body of a first passive non-linear earplug into a right ear of a subject; inserting the tapered body of a second passive non-linear earplug into a left ear of the subject; and subjecting the subject to a loud sound, wherein the two passive non-linear earplugs attenuate the loud sound before reaching the eardrums of the subject. In one aspect, the method can include subjecting the subject to low-range or mid-range sounds, wherein the two passive non-linear earplugs allow the subject to hear the low-range or mid-range sounds while the loud sounds are attenuated. In one aspect, the two passive earplugs have high insertion loss of approximately 41 dB to 45 dB when the loud sound is 168 dB. In one aspect, the two passive earplugs have low insertion loss of approximately 6 dB to 10 dB when the mid-range sound is 95 dB.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1A includes a side view of an embodiment of a passive non-linear earplug.

FIG. 3B includes a side view of an embodiment of a passive non-linear earplug.

FIG. 3C includes a side view with portions in a cross-sectional profile view of an embodiment of a passive non-linear earplug.

FIG. 4 includes a top view of an embodiment of an acoustic filter disk.

FIG. 4A includes a side view of an embodiment of a planar acoustic filter disk.

FIG. 4B includes a side view of a convex acoustic filter disk.

FIGS. 5A-5B include perspective views of an embodiment of a passive non-linear earplug.

Figure 1:
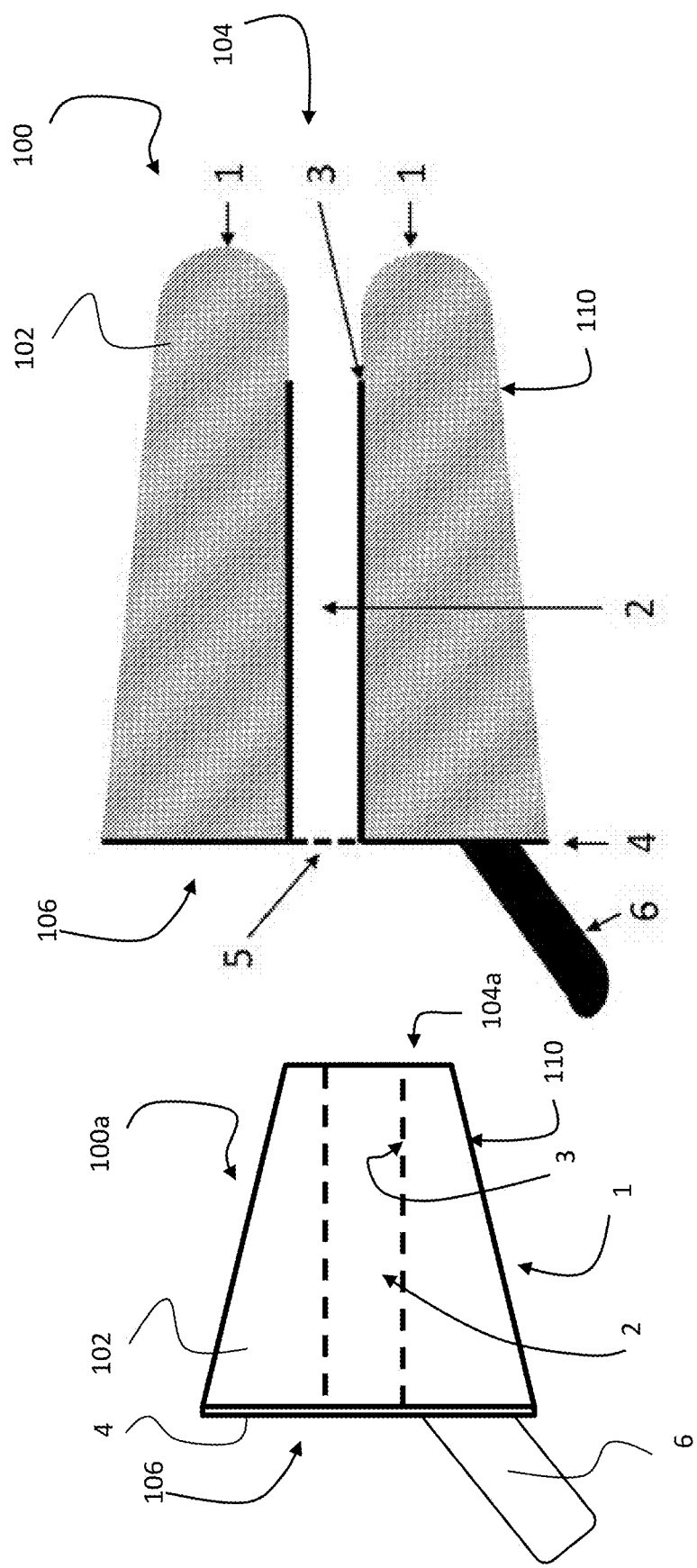
FIG. 1 includes a cross-sectional profile view of an embodiment of a passive non-linear earplug.

The embodiments illustrated in the figures are arranged in accordance with at least one of the embodiments described herein, and which arrangement may be modified in accordance with the disclosure provided herein by one of ordinary skill in the art. Each embodiment of a figure includes components that can be combined with the other embodiments of other figures.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes an earplug device and method for providing hearing protection against loud impulse noise exposure. The main application of the earplug device is to provide hearing protection when needed, such as to protect the ear from harmful loud noises that can arise from guns, artillery or blast impulse noises, while allowing regular sounds or noises (e.g., speech) to be heard as normal to maintain situational awareness. In civilian settings, similar situations may occur with fireworks and pneumatic or blast powder activated tools, shooting ranges, explosive excavations, blasting, and other industrial explosive materials use. Therefore, the earplug device can be used in methods to reduce the loud noises or sounds in the ear and inhibit the loud noises or sounds from harmfully impacting the ear drum while allowing soft or normal sounds to enter into the ear and impact the ear drum in a normal hearing manner.

Figure 6:
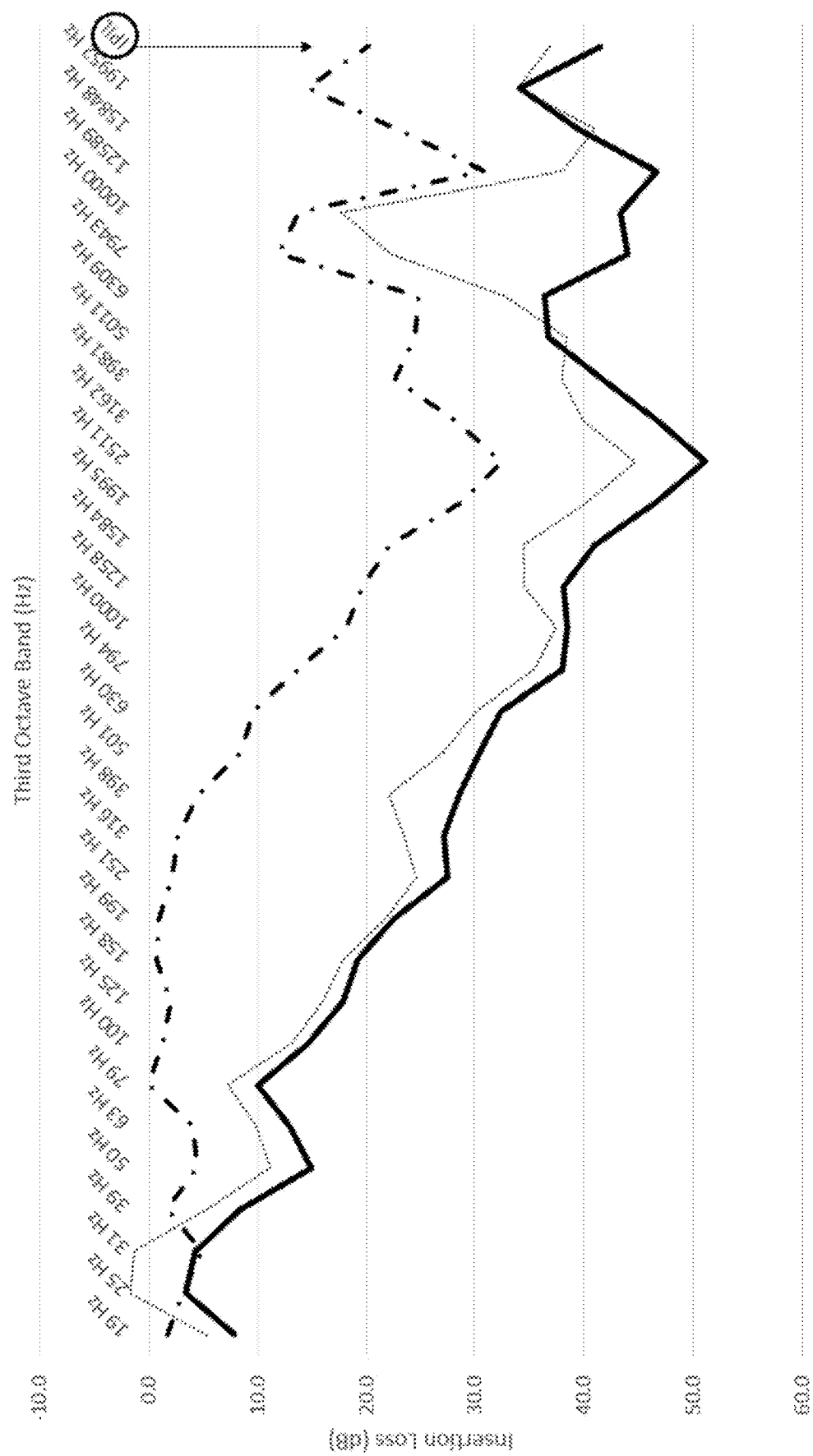
FIG. 6 shows the impulsive peak insertion loss at 168 dB for the present invention (e.g., solid line) compared to comparative devices.

In one embodiment, the earplug device includes a passive non-linear earplug for blocking very loud sounds (e.g., gun fire, blast, artillery, industrial explosives, etc.) while other sounds (e.g., soft or normal sounds) are allowed to pass through and be heard by the wearer. The earplug device is configured with components that function as a nonlinear (e.g., sound level-dependent) earplug which attenuates more sound as the sound exposure level becomes higher. The earplug device does not include any automatic, electronic or actuated moving parts, and thereby is a passive earplug. While the earplug can be worn in an ear by any subject that wants to inhibit loud sounds from harming their ear, the passive non-linear earplug described herein may be particularly useful for subjects in the military, police, and certain sports (e.g., hunting, shooting) where loud impulse sounds are present, but where a good situational awareness is important to the subject. The passive non-linear earplug is configured as a simple device with a surprisingly and unexpectedly high (e.g., best-in-class) impulse peak insertion loss (IPIL) performance rating. FIG. 6 shows the impulsive peak insertion loss at 168 dB for the present invention (e.g., solid line) compared to comparative devices, which shows the present invention is significantly improved. Due to its simplicity, the passive non-linear earplug device is relatively easy to fabricate with few components and has a low cost. The low cost can increase compliance and use, which can result in more subjects retaining their hearing and inhibiting hearing loss in subjects that are exposed to loud sounds. It is also surprising and unexpected that such a high IPIL achieved by the passive non-linear earplug also allows for normal sounds to be heard by the subject.

Ear protection devices are customarily rated with the Noise Reduction Rating (NRR), which is an estimate of the reduction of noise at the ear when protectors are worn properly. A typical rating may be 20 dB to 30 dB for most earplugs, and is a useful rating for low and medium sound levels. Specifically, for loud impulse noises with durations of a few milliseconds, the new American National Standards Institute (ANSI) S12.42 standard was created in 2010 to quantify the attenuation of non-linear behavior at high sound levels. This standard uses three levels of impulsive noises, with peak values at nominally 132 dB, 150 dB, and 168 dB. This rating number is the IPIL. Since the introduction of the new standard, several papers have been published with IPIL ratings for commercially available earplugs (see, [1][2][3]). Those earplugs typically have an IPIL rating of 20 dB to 30 dB, with the best designs reaching approximately 35 dB. This includes state-of-the-art commercial and military grade earplugs, ear muffs and electronic earplug devices. However, it has been found that the passive non-linear earplug described herein provides an IPIL that is improved over prior sound attenuation devices, especially other passive non-linear earplugs.

In one embodiment, the embodiments of passive non-linear earplugs provide hearing protection with an IPIL rating of approximately 41 dB to 45 dB at 168 dB sound level. In the past, this performance level was typically reached only when two hearing protectors were used in combination, such as an earplug and ear muff. Furthermore, this impulse performance is combined with a very low insertion loss at low sound levels, such as approximately 6 dB to 10 dB at 95 dB sound level. This demonstrates a very high non-linearity of the earplug, and will allow optimal situational awareness by the subject wearing the passive non-linear earplugs described herein, while protecting against loud impulse noises, such as gun shots and blast events.

As an example, impulsive noises can have the following peak levels: explosions about 150 dB to about 195 dB; Gunshots about 140 dB to about 180 dB; hammer forge about 130 dB to about 155 dB; fireworks about 125 dB to about 160 dB; pneumatic tools about 120 dB to about 145 dB; hammering about 110 dB to about 140 dB; rock concerts about 100 dB to about 125 dB; and drums about 100 dB to about 150 dB. Accordingly, a subject may wear the passive non-linear earplugs described herein during any of these sound events while maintaining the ability to carry out a normal volume conversation or to otherwise be situationally aware of sounds other than the loud sounds (e.g., impulsive noises). Accordingly, there is high impact noise attenuation at higher dB values, and lower noise attenuation at lower dB values.

Figure 2:
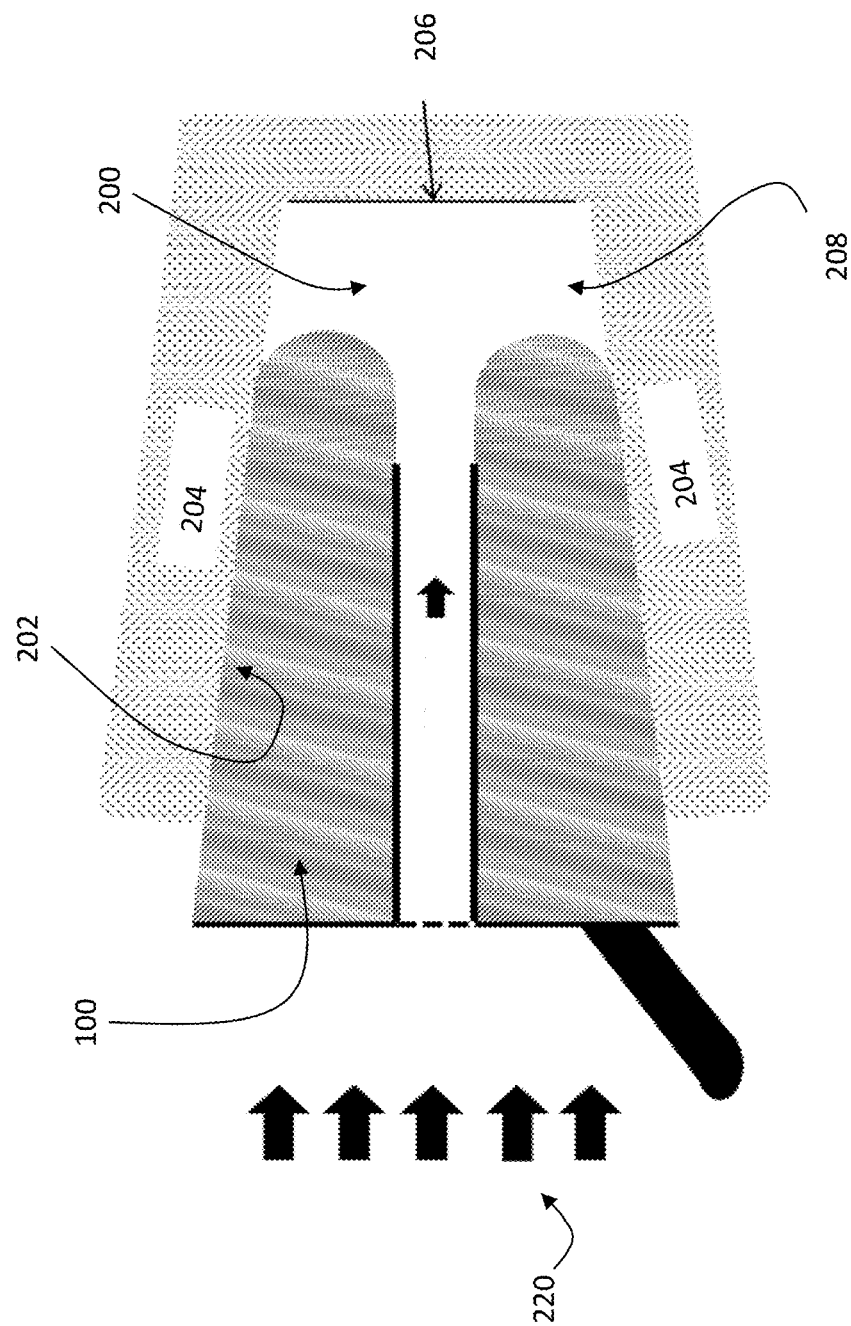
FIG. 2 shows a cross-sectional profile view of an embodiment of a passive non-linear earplug being inserted into an ear canal.

FIG. 1 shows the basic embodiment of the passive non-linear earplug device 100 (referred to herein as the earplug 100). FIG. 1 is a cross-sectional profile view. The earplug 100 is shown to include a tapered structure 102 (ear piece) that has a tapered cylindrical shape 1. The tapered structure 102 can be prepared of an elastomeric or foam material, or any other sound dampening material that has shape memory properties. The earplug 100 is shaped and sized to fit into the ear canal, as shown in FIG. 2. The earplug 100 includes a sound channel 2 extending from a proximal end 104 (e.g., insertion end) to a distal end 106 (e.g., exposed end), which sound channel 2 is the channel that allows sound to come through to the ear drum or tympanic membrane. While the sound channel 2 is shown to be located centrally of the tapered structure 102, the sound channel 2 can be in an asymmetric position (e.g., not central), and may be along a longitudinal axis (e.g., central longitudinal axis) or at an angle relative to the longitudinal axis.

The sound channel 2 is a lumen that is at least partially lined with a structural tube 3 so that the sound channel 2 does not collapse and remains open. The structural tube 3 is prepared from a material that does not collapse when the tapered structure is compressed for insertion into the ear, and thereby the structural tube 3 may be prepared of a plastic material. The structural tube 3 is shown to have an end at the distal end 106 and extend toward the proximal end 104; however, the structural tube 3 may have ends at any points between the distal end 106 and proximal end 104, or may have an end at the proximal end 104 and extend to the distal end 106, or extend fully from the distal end 106 to proximal end 104.

The earplug 100 can include an acoustic filter 4, which can be shaped as a thin disk. The acoustic filter 4 can be applied to the distal end 106 of the tapered structure 102. The acoustic filter 4 includes one or more small holes 5, which can be located at the center of the disk such that the holes 5 are aligned with the sound channel 2. In one aspect, there are two or more of the small holes 5 in the acoustic filter 4 that are aligned with the sound channel 2. The small holes 5 extend all the way through the acoustic filter 4 from one side to the other so as to fluidly couple the environment on the distal end 106 with the sound channel 2. The material of this acoustic filter 4 can be any material, where examples can be metal or plastic. In one aspect, the acoustic filter 4 is made from stainless steel, but other materials (e.g. various molded plastics) can be used as well. The positioning of the holes 5 in the acoustic filter 4 and the spacing of the holes 5 with respect to each other and/or to the sound channel 2 is not critical as long as the holes 5 are open to the sound channel 2 and not obstructed by the tapered structure 102.

As shown in FIG. 1, the earplug 100 can include a handle 6, which is configured and dimensioned so that fingers can grip the handle 6 for insertion and withdrawal of the earplug 100 into and out from the ear. The handle 6 is attached to the distal end 106 of the earplug 100, or it can be coupled or integrated with the acoustic filter 4. In another alternative, the acoustic filter 4 may have an aperture that the handle 6 protrudes through, and where the handle 6 may be made of the same material as the tapered structure 102 (e.g., integrated as a unitary piece) or coupled thereto. While the handle 6 is shown to be a member, the handle 6 may be in the form of a cord or any other suitable mechanism that can be used for insertion and/or extraction. In one aspect, the handle 6 can be as disclosed in U.S. Pat. No. 8,671,948, which is herein incorporated by reference in its entirety.

The structural tube 3 can be a plastic tube having a lumen and an outside surface that lines the sound channel 2. This structural tube 3 allows for the earplug 100 to be compression fitted by squeezing the tapered structure 102 for insertion into the ear where the structural tube 3 does not allow for the sound channel 2 to collapse, and thereby the sound channel 2 remains open upon insertion of the earplug 100 and wearing in the ear. This allows the earplug 100 to be made of a foam or other similar material that can have shape memory to allow for compression and automatic return to shape. If desired, the shape of the foam ear piece, such as the tapered structure, can be replaced by any suitable ear piece shape, for example a polymeric multiple flange earpiece as disclosed in U.S. Pat. No. 4,867,149, which is herein incorporated by reference in its entirety.

In an example, the size of the tapered structure 102 can be optimized to fit inside the ear canal, whether the user is an infant, child, teenager, or adult. This means that the outer diameter on the narrow end (e.g., proximal end 104) is around 0.35" while the diameter on the widest end (e.g., distal end 106) is around 0.4". The inside diameter of the sound channel 2 is around 0.125", and the length of the sound channel 2 is around 0.6". The outer diameter of the structural tube 3 is around 0.125" and the inner diameter of the lumen of the structure tube is around 0.1". The length of the structural tube 3 can range from 0.2" to 0.6", or from 0.3" to 0.5" or about 0.4". The thickness of the disc of the acoustic filter can range from 0.0001" to about 0.01";

however, the thickness can be any reasonable dimension. However, it should be recognized that these dimensions of the different aspects of the earplug 100 may be modified and varied, such as by 1%, 2%, 5%, 10%, 20%, 25%, or up to 50%, for example.

FIG. 1A shows another embodiment of the earplug 100a. Here, instead of the proximal end 104a having a rounded shape from the outside surface 110 to the sound channel 2, the proximal end 104a is flat and has corners to the outside surface 110. Any other surface may also be rounded and any corners may also be rounded corners. Such designs are within the scope of this disclosure.

FIG. 2 shows the earplug 100 being inserted into an ear canal 200. As shown, the outside surface 110 of the earplug 100 presses against the surface 202 of ear canal tissue 204 in a position such that there is a gap 208 between the proximal end 104 and the ear drum 206. Accordingly, incoming sound 220 having high peak level dB reaches the earplug 100 and enters through the holes 5 of the acoustic filter 4 and enters into the lumen of the structural tube 3/sound channel 2 as attenuated sound that has significantly less high peak level dB.

Figure 3A:
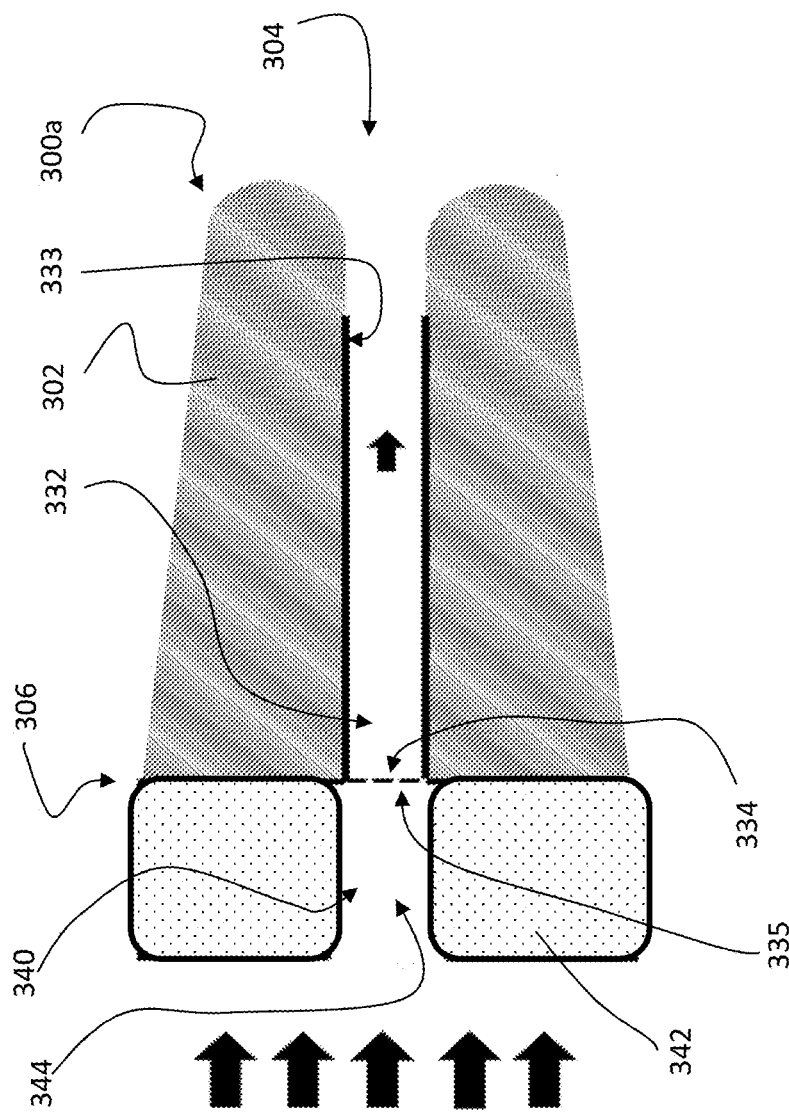
FIG. 3A includes a cross-sectional profile view of an embodiment of a passive non-linear earplug.

FIGS. 3A-3C show several embodiments of the passive non-linear earplug. These figures show different embodiments of an external sound channel that is fluidly coupled with the internal sound channel.

FIG. 3A shows an embodiment of the passive non-linear earplug device 300a (referred to herein as the earplug 300a). FIG. 3A is a cross-sectional profile view. The earplug 300a is shown to include a tapered structure 302 (ear piece) that has a tapered cylindrical shape. The earplug 300a is shaped and sized to fit into the ear canal, as shown in FIG. 2. The earplug 300a includes an internal sound channel 332 extending from a proximal end 304 (e.g., insertion end) to a distal end 306 (e.g., exposed end) of the tapered structure. The internal sound channel 332 is a lumen that is at least partially lined with a structural tube 333 so that the internal sound channel 332 does not collapse and remains open. The earplug 300a can include an acoustic filter 334, which can be shaped as a thin disk, located on the distal end 306 of the tapered structure 302. The acoustic filter 334 includes one or more small holes 335, which can be located at the center of the disk such that the holes 335 are aligned with the sound channel 332. An external sound channel 340 is formed by an annular member 342 with an aperture 344 being coupled to the distal end 306 of the tapered structure 302. The annular member 342 may be formed of the same type of material as the tapered structure 302 or it may be a hard material, such as a plastic. The external sound channel 340 receives the incoming sound and causes some attenuation before it reaches the acoustic filter 334.

FIG. 3B shows an earplug 300b similar to the earplug 300a of FIG. 3A; however, the aperture 344 of the annular member 342 is larger so that the external sound channel 340 is wider than the internal sound channel 332. FIG. 3B is a side view with portions shown in cross-section. Also, an external acoustic filter 346 may be located on the distal end 348 of the annular member 342 to provide further sound attenuation prior to entering into the external sound channel 340.

FIG. 3C shows an embodiment of an earplug 300c, where the structural tube 350 includes an end 352 with holes 354, and where the structural tube 350 is located midway in the sound channel 332 so as to effectively create an external sound channel 356 and internal sound channel 358. FIG. 3C is a side view with portions shown in cross-section. The structural tube 350 having the end 352 with holes 354 may be considered to be a tubular acoustic filter 360, which functions as the structural tube and acoustic filter. Also, while only one tubular acoustic filter 360 may be used, three different ones are shown in the earplug 300c of FIG. 3C; however, it should be recognized that any number of such tubular acoustic filters 360 may be used. Additionally, a tubular acoustic filter 360 may include both ends having the holes 354, which is shown in the distal tubular acoustic filter 360, and which may be a tubular double acoustic filter.

Additionally, it should be recognized that the components embodiments of FIGS. 3A-3C may be combined or modified in accordance with the skill of one of ordinary skill in the art.

Figure 3D:
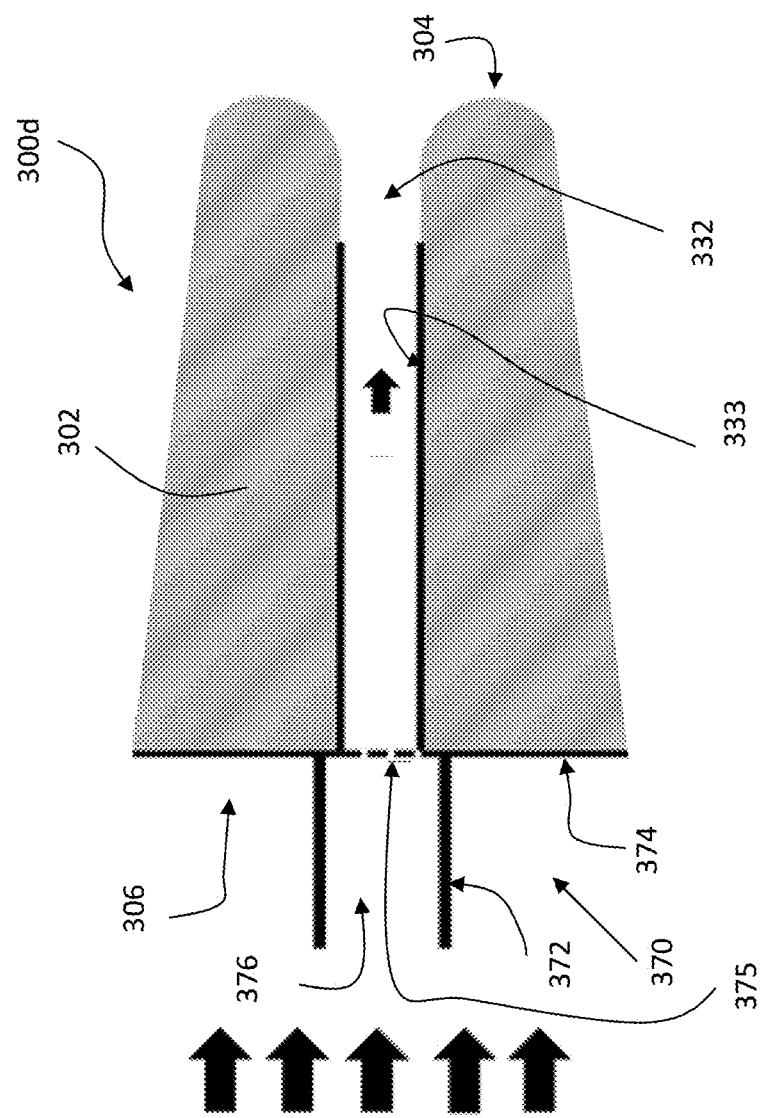
FIG. 3D includes a cross-sectional profile view of an embodiment of a passive non-linear earplug.

FIG. 3D shows an embodiment of the passive non-linear earplug device 300d (referred to herein as the earplug 300d). FIG. 3D is a cross-sectional profile view. The earplug 300d is shown to include a tapered structure 302 (ear piece) that has a tapered cylindrical shape. The earplug 300d is shaped and sized to fit into the ear canal, as shown in FIG. 2. The earplug 300d includes an internal sound channel 332 extending from a proximal end 304 (e.g., insertion end) to a distal end 306 (e.g., exposed end) of the tapered structure 302. The internal sound channel 332 is a lumen that is at least partially lined with a structural tube 333 so that the internal sound channel 332 does not collapse and remains open. The earplug 300d can include an acoustic filter cap 370, which includes a thin filter disk 374, located on the distal end 306 of the tapered structure 302. The acoustic filter cap 370 includes one or more small holes 375 in the disk 374, which can be located at the center of the filter disk 374 such that the holes 375 are aligned with the internal sound channel 332. An external sound channel 376 is formed by a filter tube 372 extending from the filter disk 374, such as by being integrated or coupled. The acoustic filter cap 370 may be formed of the same type of material as the acoustic filter or structural tube 333 or a combination thereof, and it may be a hard material, such as a plastic. The external sound channel 376 receives the incoming sound and causes some attenuation before it reaches the internal sound channel 332.

Figure 3E:
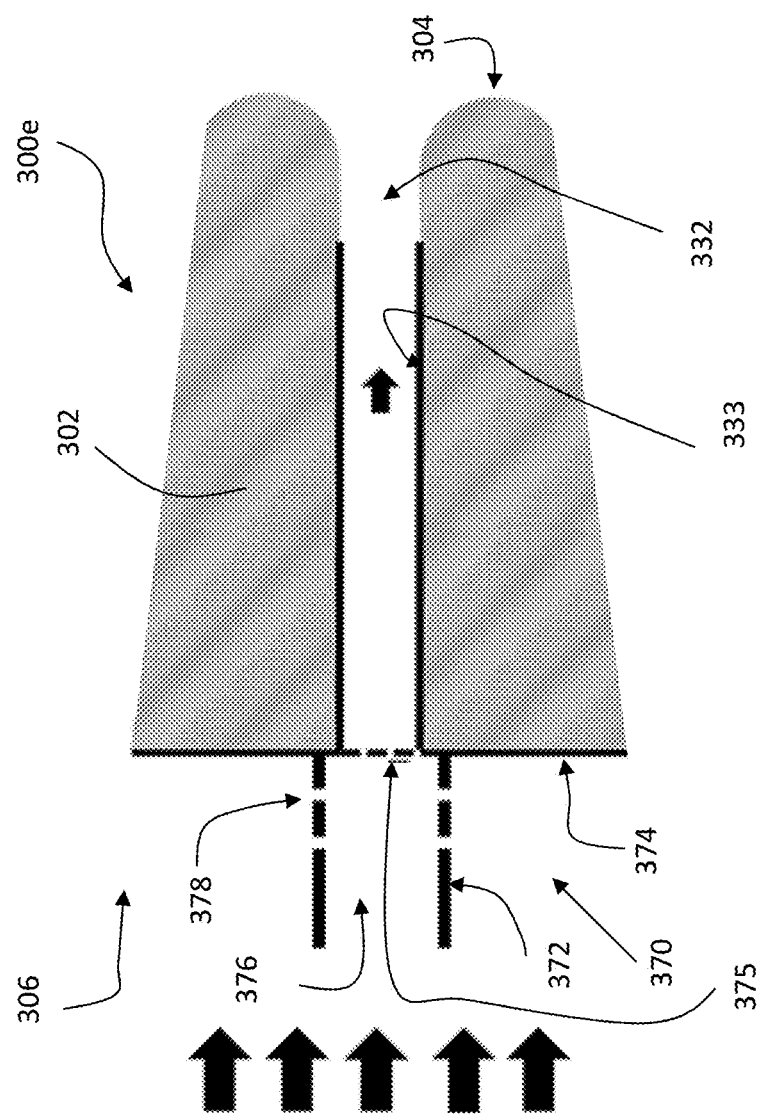
FIG. 3E includes a cross-sectional profile view of an embodiment of a passive non-linear earplug.

FIG. 3E shows an embodiment of a passive non-linear earplug device 300e (hereinafter earplug 300e) that is similar to the embodiment of FIG. 3D. However, the acoustic filter cap 370 includes the filter tube 372 having holes 378 that extend therethrough. The holes 378 provide additional filtering of the incoming sound prior to entering the internal sound channel 332. It was found that the earplug 300e improves the IPIL performance relative to the earplug 300d of FIG. 3D, however, and results in a 15% reduction of performance (compared to a fully exposed disk; e.g., disk 4, disk 402, or acoustic filter 400 of the figures).

While the embodiments of the earplugs in FIGS. 3A-3E do not show a handle, the handle may be optionally included in these embodiments. However, the filter tube 372 of the acoustic filter cap 370 may be used as a handle. Also, the holes may be considered to be perforations or apertures.

FIGS. 4-4A show that the acoustic filter 400 can include a disk 402 that is planar. As such, the incoming impulsive sound wave will reflect off the disk 402, and may further dissipate the energy of the sound wave. Alternatively, the disk 402 may be non-planar (convex, concave, or other) to optimize incoming sound wave dissipation or have a distal surface 404 (e.g., exposed surface) that is non-planar as shown in FIG. 4B.

In FIG. 4, the acoustic filter 400 is a thin perforated disk with a thickness of 0.0005" to 0.005", and with small holes 406 ranging from 0.003" to 0.02". The spacing of the holes 406 is arbitrary, but at least some of the holes must be unobstructed by the tapered foam structure and open to the cylindrical sound channel. A preferred embodiment of the device has a disk thickness of 0.00197", and one hole with a diameter of 0.00984". This results in an IPIL of 41.5 dB. Reducing the hole diameter to 0.00787" result in an IPIL of 42 dB, while having two holes with diameters of 0.00984" and 0.00787" results in an IPIL of 40.5 dB. To get this level of performance the acoustic filter 400 is not embedded or recessed in a channel on the "impulse sound" side, instead the acoustic filter 400 is on the distal end. Many patent disclosures, e.g., U.S. Pat. Nos. 6,148,821, 7,697,706, and 8,054,985 have such a feature, but it reduces the IPIL performance of our device significantly (around −20%). As such, the acoustic filter 400 can cover the distal end of the earplug, or at least 75%, 85%, 95%, or 99%, excluding the hole of the internal sound channel.

Figure 5:
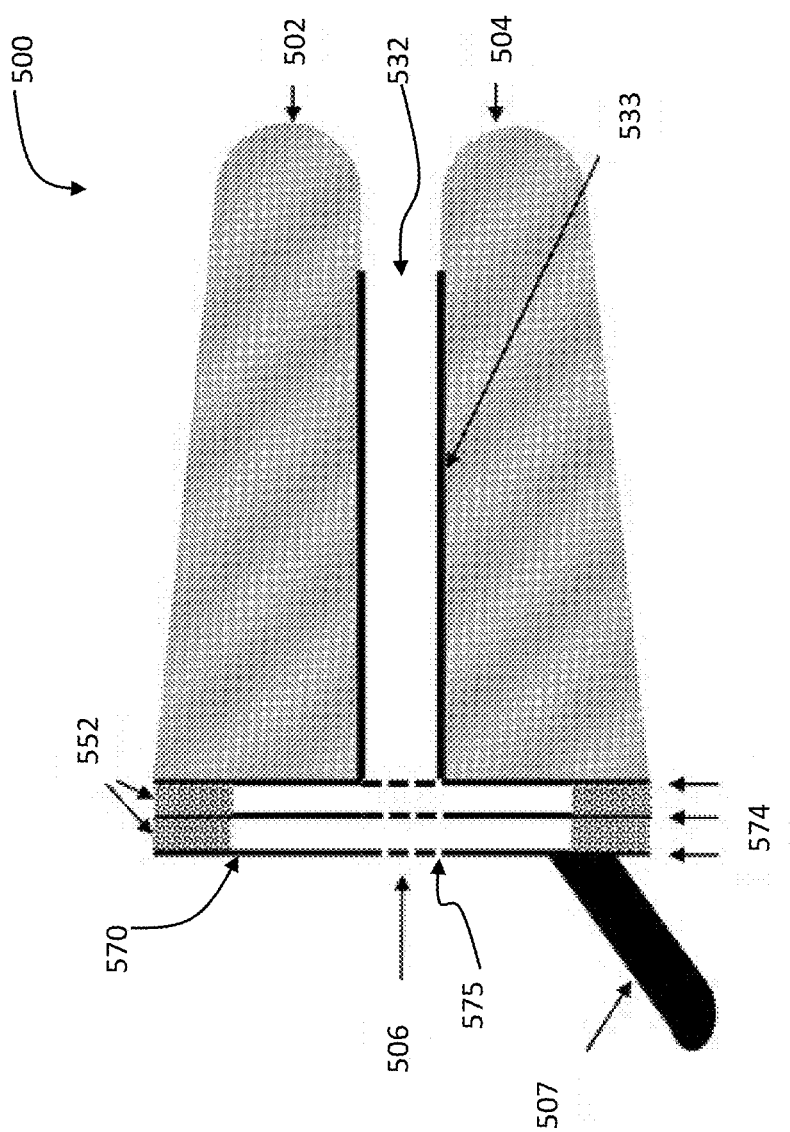
FIG. 5 includes a cross-sectional profile view of an embodiment of a passive non-linear earplug.

FIG. 5 shows an embodiment of the earplug 500 with two tuning elements attached to the acoustic filter disk 574 and earplug body 502. FIG. 5 is a cross-sectional profile view. The earplug 500 is shown to include the earplug body 502 (ear piece with tapered structure) that has a tapered cylindrical shape. The earplug 500 is shaped and sized to fit into the ear canal, as shown in FIG. 2. The earplug 500 includes an internal sound channel 532 extending from a proximal end 504 (e.g., insertion end) to a distal end 506 (e.g., exposed end) of the earplug body 502. The internal sound channel 532 is a lumen that is at least partially lined with a structural tube 533 so that the internal sound channel 532 does not collapse and remains open. The earplug 500 can include an acoustic filter cap 570 located on the distal end 506 of the earplug body 502. The acoustic filter cap 570 includes a plurality of acoustic filter disks 574, where three filter disks 574 are shown. Each filter disk 574 includes one or more small holes 575 therethrough, which small holes 575 can be located at the center of the filter disk 574 such that the holes 575 are aligned with the internal sound channel 532. The holes 575 of one filter disk 574 may be aligned or not aligned with the holes 575 of the adjacent filter disk 574.

In one embodiment, each acoustic filter cap 570 includes a plurality of acoustic filter disks 574, such as a perforated disk, separated by an annular ring 552 (e.g., two annular rings 552 are shown). The annular ring 552 may be made from plastic, metal, or foam, and may be the same or different material from the disks 574. The space between the disks 574 forms a Helmholtz resonator and the earplug performance can be tuned in the frequency spectrum that way. By having the acoustic filter disks 574 in series, a higher IPIL performance of 45 dB can be reached. The embodiment of FIG. 5 has three disks with at least one hole 575, each hole 575 having a diameter of 0.00787". The annular ring 552 has a thickness of 0.095" with an inner diameter of 0.145", while the outer diameter is the same as the disk 574's outer diameter. The acoustic filter cap 570 includes all of the acoustic filter disks 574 and annular rings 552. In one aspect, the acoustic filter cap 570 may also have the structural tube 533 attached thereto; however, the structural tube 533 may be separate. The annular rings 552 may be attached to the disks 574 with adhesive, or each annular ring 552 may be integrated with one or more disks 574, or vice versa. Additionally, an optional handle 507 is shown.

FIGS. 5A-5B show the earplug 500 with the earplug body 502 being separate and connectable with the acoustic filter cap 570. The acoustic filter cap 570 can be inserted into the sound channel 532 and withdrawn therefrom. It should be recognized that the acoustic filter cap 570 can include one or more filter disks 574 having the one or more holes 575, where two or more filter disks 574 would be separated from each other by the annular rings 552.

The earplugs described herein may be provided as manufactured articles. Alternatively, the earplugs may be provided with the tapered earplug body and the acoustic filter cap with the structural tube separate, so that they can be combined for use. In one aspect, the earplugs can be provided with a plurality of earplug bodies for each ear along with one acoustic filter cap for each ear, which allows for the acoustic filter cap to be reused with a number of tapered earplug bodies. As such, after a tapered earplug body is used, and possibly damaged or soiled, the acoustic filter cap can be removed and inserted into a new tapered earplug body.

In one embodiment, the earplugs can be manufactured by providing the tapered earplug body, providing the acoustic filter cap, and coupling the acoustic filter cap to the earplug body. In one aspect, adhesive is provided and coated on the acoustic filter cap and/or earplug body prior to the coupling.

In one embodiment, the acoustic filter cap can be manufactured by providing two or more acoustic filters, providing one or more annular rings, and then coupling the one or more annular rings to the two or more acoustic filters as shown in FIG. 5. In one aspect, the structural tube can be provided and inserted into the sound channel with or without adhesive. In one aspect, the filter disks, handle and annular rings can be provided as separate components and glued or compression fitted together. However, the filter disks, optional handle and annular rings can be manufactured as one piece and either made from plastic, metal, glass, or ceramic materials or combinations thereof. In another aspect, the filter disks, handle, annular rings and structural tube can be manufactured as one piece and either made from plastic, metal, glass, or ceramic materials or combinations thereof. In this embodiment, a tapered earplug body is compression fitted (or glued) to the acoustic filter cap having the filter disks, optional handle, annular rings and structural tube.

In one embodiment, a hearing protection device, intended to be inserted into the ear canal, can include: a tapered foam structure (e.g., ear piece) with a cylindrical channel where the narrow end of the tapered foam structure is configured to be inserted into the ear canal until it fits snugly; and a passive non-linear acoustic filter that is mounted on the wide end of the tapered foam structure. In one aspect, the passive non-linear acoustic filter can include a series of zero, one or more passive tuning elements and filters put in series and attached to the non-linear acoustic filter. In one aspect, a handle or string for removing the earplug from the ear canal is attached to the tapered foam structure and/or passive non-linear acoustic filter. In one aspect, the tapered foam structure (ear piece) is constructed from any suitable foam (e.g., polystyrene) or memory foam (e.g. polyurethane). In one aspect, the tapered foam structure (ear piece) comfortably fits the ear canal. The foam structure is a tapered cylindrical shape and sized to fit into the ear canal. This means that the diameter on the narrow end is around 0.35" while the diameter on the widest side is around 0.4". The inside diameter is around 0.125", and the length of the ear piece is around 0.6". Other sizes can be accommodated as well to fit large, medium or small ear canals. In one aspect, the tapered foam structure (ear piece) has an inner plastic liner within the cylindrical channel. In one aspect, the non-linear acoustic filter includes an ultra-thin perforated disk with one or more small holes. In one aspect, the acoustic disk is a mesh disk. In one aspect, the disk is made from any type of metal or alloy (e.g. stainless steel, aluminum, etc.), glass, ceramic or plastic (e.g. nylon, polyethylene, polyvinyl chloride, polycarbonate, polypropylene, polyurethane, polyoxmethylene, or silicon).

In one embodiment, the acoustic disk is fully external to the earplug body so as to be fully exposed to the incoming sound and thereby the acoustic filter is not embedded or recessed in a channel on the "incoming sound" side. That is, the acoustic disk is on a distal end on the outside of the earplug body. In one aspect, the surface of the acoustic disk that is on the "incoming sound" side is planar or some other shape (e.g., convex, concave, or irregular surface bumps/textured) to reflect incoming sound waves. In one aspect, the disk diameter is the same (or nearly the same) to the diameter of the distal end of the earplug body. In one aspect, the disk has a thickness of 0.0005" to 0.005", and with small holes ranging from 0.003" to 0.02". The spacing of the holes is arbitrary, but at least some of the holes must be unobstructed by the tapered foam structure cylindrical sound channel.

In one embodiment, zero, one or more tuning element(s) are attached to the earplug body or acoustic disc. Each tuning element includes an annular ring and an acoustic disk with one or more holes that align with the sound channel of the earplug body, where the annular rings may or may not include adhesive between each annular ring and adjacent acoustic disc(s). In one aspect, each tuning element includes a disk having an annular ring attached to a flat surface thereof. In one aspect, the annular ring is made from any foam, plastic, or metal. In one aspect, the annular ring has an inner diameter of 0.005" to 0.4". The outside diameter of the annular ring is usually chosen to be the same as the outside diameter of the disk.

In one embodiment, the hearing protection device has non-linear acoustic attenuation, with low attenuation for low-range (e.g., less than 80 dB) and mid-range (e.g., about 80-120 dB) sounds and high attenuation for loud sounds (e.g., higher than or about 120 dB).

In one embodiment, a hearing protection method is performed by inserting a hearing protection device into the ear canal. In one aspect, the hearing protection method can include: receiving incident acoustic energy from the environment via the passive non-linear filter to prevent load sounds reaching the inner ear; incoming acoustic energy is reflected off a disk and remaining energy must propagate through a set of small holes in the passive non-linear filter. Both effects are highly acoustic energy dissipative for loud noises. Attenuation level is sound level dependent with low-range and mid-range sounds traversing the hearing protection device while the high-range loud sounds are attenuated. For loud impulse noises (gun, blast, machinery) there is a high level of attenuation. For low level noise or sound (conversation level) there is minimal or no attenuation. Thus, optimal situational awareness and sound localization ability are maintained.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

1] WJ Murphy, Measurement of impulse peak insertion loss for four hearing protection devices in field conditions, International Journal of Audiology 2012; 51: S31-S42.

[2] A Nakashima, Comparison of different types of hearing protection devices for use during weapons firing, Journal of Military, Veteran and Family Health, 1(2) 2015 doi: 10.3138/jmvfh.3076.

[3] A Khan, Comparison of Two Acoustic Test Fixtures for Measurement of Impulse Peak Insertion Loss, EPHB Report No. 350-13a, NIOSH

The invention claimed is:

1. A passive non-linear earplug comprising:
an earplug body having a tapered configuration that is wider at a distal end and narrower at a proximal end, wherein the proximal end is an insertion end and the distal end is an exposed end, and having a channel extending from a distal channel opening formed in a distal end external surface of the distal end of the earplug body to a proximal channel opening formed in a proximal end surface of the proximal end of the earplug body, the earplug body being formed from a shape-memory material and having a shape and a size adapted for being received into an ear canal of a human subject such that, during use, an outside surface of the earplug body presses against tissue surfaces in the ear canal, wherein the distal end external surface is a wider surface than the proximal end surface; and
an acoustic filter having a filter body shaped as a thin planar disk attached to the distal end of the earplug body so as to be outside of the earplug body, the disk being sized and positioned on the earplug body to cover at least 75% of the distal end external surface of the earplug body, the disk having a first disk surface facing the distal end external surface of the earplug body, the disk covering the distal channel opening, the disk having a second disk surface facing away from the distal end external surface, and the disk having one or more holes extending from the first disk surface to the second disk surface such that the one or more holes are aligned with the distal channel opening of the earplug body.

2. The earplug of claim 1, wherein the one or more holes extending from the first disk surface to the second disk surface have a diameter ranging from 0.003 inches to 0.02 inches.

3. The earplug of claim 2, wherein the disk has a thickness of 0.0005 inches to 0.005 inches.

4. The earplug of claim 3, wherein the one or more holes are circular and the channel has a constant inside diameter from the distal channel opening in the distal end external surface to the proximal channel opening of the earplug body.

5. The earplug of claim 3, wherein the channel has an inside diameter of about 0.125 inches.

6. The earplug of claim 1, further comprising a structural tube member coupled to the earplug body by being located in the channel, wherein the structural tube member has a uniform inner diameter from a structural tube distal end to a structural tube proximal end, wherein the structural tube member has a diameter that is smaller than a diameter of the channel and a diameter of the disk.

7. The earplug of claim 6, wherein the structural tube member is integrated with the disk by the structural tube member extending from the first disk surface into and through the distal channel opening of the channel.

8. The earplug of claim 1, further comprising a tube member having a proximal end opening in a proximal end and a distal end opening in a distal end, wherein the distal end is integrated with the first disk surface of the disk body and the proximal end is located in the channel of the earplug body, the tube member being an elongated tube having a lumen extending from the distal end opening to the proximal end opening that aligns with the channel, wherein the tube member has a diameter that is smaller than a diameter of the channel and a diameter of the disk.

9. The earplug of claim 8, wherein the tube member includes a plurality of lateral apertures extending through a tube member body from a tube member external surface to the lumen.

10. The earplug of claim 1, wherein the disk includes a proximal side that is attached to the earplug body so as to be external to the earplug body, and the disk includes a distal side, the earplug further comprising:
an annular ring having a proximal side attached to the distal side of the disk so that an aperture of the annular ring surrounds the one or more holes of the disk; and
a second disk attached to a distal side of the annular ring to form a cavity outside of the earplug body that is between the disk and the second disk, the second disk having one or more second holes aligned with the distal channel opening such that the annular ring surrounds the one or more second holes of the second disk.

11. The earplug of claim 10, further comprising:
a second annular ring having a proximal side attached to a distal side of the second disk so that a second aperture of the second annular ring surrounds the one or more second holes of the second disk; and a third disk attached to a distal side of the second annular ring to form a cavity outside of the earplug body that is between the second disk and third disk, the third disk having one or more third holes aligned with the distal channel opening such that the second annular ring surrounds the one or more third holes of the third disk.

12. The earplug of claim 1, further comprising a handle attached to the disk.

13. The earplug of claim 1, wherein the first disk surface and second disk surface are planar surfaces.

14. A method of hearing protection comprising:
providing two of the passive non-linear earplugs of claim 1;
inserting the earplug body of a first passive non-linear earplug into a right ear of a subject;
inserting the earplug body of a second passive non-linear earplug into a left ear of the subject; and
subjecting the subject to a loud sound, wherein the two passive non-linear earplugs attenuate the loud sound before reaching eardrums of the subject.

15. The method of claim 14, further comprising subjecting the subject to low-range or mid-range sounds, wherein the two passive non-linear earplugs are configured to allow the subject to hear the low-range or mid-range sounds while loud sounds are attenuated.

16. The method of claim 15, wherein the two passive non-linear earplugs have high insertion loss of approximately 41 dB to 45 dB when the loud sound is 168 dB.

17. The method of claim 15, wherein the two passive non-linear earplugs have low insertion loss of approximately 6 dB to 10 dB when the mid-range sound is 95 dB.

18. A kit comprising:
a plurality of the passive non-linear earplugs of claim 1.

19. The kit of claim 18, wherein each passive non-linear earplug comprises a structural tube member coupled to the earplug body by being located in the channel, wherein the structural tube member has a uniform inner diameter from a structural tube distal end to a structural tube proximal end, wherein the structural tube member has a diameter that is smaller than a diameter of the channel and a diameter of the disk.

20. The kit of claim 19, wherein the structural tube member is integrated with the disk by the structural tube member extending from the first disk surface into and through the distal channel opening of the channel.

* * * * *